United States Patent
Spittelmeister et al.

(10) Patent No.: US 9,803,756 B2
(45) Date of Patent: Oct. 31, 2017

(54) DEVICE FOR CONTROLLING FLUID MEDIA AND USE OF A MOLDED PART IN SUCH A DEVICE

(71) Applicant: ASCO NUMATICS GMBH, Oelbronn-Duerrn (DE)

(72) Inventors: Uwe Spittelmeister, Ettlingen (DE); Felix Ams, Kaempfelbach (DE)

(73) Assignee: ASCO NUMATICS GMBH, Oelbronn-Duerr (DE)

( * ) Notice: Subject to any disclaimer, the term of this patent is extended or adjusted under 35 U.S.C. 154(b) by 14 days.

(21) Appl. No.: 14/922,508

(22) Filed: Oct. 26, 2015

(65) Prior Publication Data
US 2016/0123480 A1 May 5, 2016

(30) Foreign Application Priority Data
Oct. 29, 2014 (EP) .................................... 14190865

(51) Int. Cl.
| | |
|---|---|
| *F16K 7/02* | (2006.01) |
| *F16K 11/02* | (2006.01) |
| *F16K 27/00* | (2006.01) |
| *F16K 31/06* | (2006.01) |
| *A61M 39/28* | (2006.01) |
| *F16K 25/00* | (2006.01) |
| *F16K 27/02* | (2006.01) |

(Continued)

(52) U.S. Cl.
CPC ............ *F16K 11/022* (2013.01); *F16K 7/045* (2013.01); *F16K 25/005* (2013.01); *F16K 27/0236* (2013.01); *F16K 27/0263* (2013.01); *F16K 31/0624* (2013.01); *F16K 31/10* (2013.01); *A61M 5/14* (2013.01)

(58) Field of Classification Search
CPC .. A61M 39/28; A61M 39/284; A61M 39/286; F16K 11/027; F16K 27/0236; F16K 27/0263; F16K 31/0624; F16K 7/045; F16K 7/066; Y10T 137/87716; Y10T 137/87772; Y10T 137/87877
USPC ........................................................ 251/7, 9
See application file for complete search history.

(56) References Cited

U.S. PATENT DOCUMENTS 3,411,534 A * 11/1968 Rose ..................... A61M 39/28
137/595
3,638,681 A *  2/1972 Moore ..................... F16K 7/04
137/606

(Continued)

FOREIGN PATENT DOCUMENTS

| DE | 10 2010010827 | 9/2011 | |
|---|---|---|---|
| DE | 102011011578 A1 * | 8/2012 | ......... F16K 31/0624 |

(Continued)

*Primary Examiner* — Seth W Mackay-Smith
(74) *Attorney, Agent, or Firm* — Michael J. Striker (57) ABSTRACT

A device for controlling fluid media, such as a directional control valve, includes a molded part made from an elastomeric material in which at least one line section is formed. The line section connects at least two connections to one another, between which at least one flow path extends. The device or valve has a control unit that includes an actuator coupled to at least one blocking element. The at least one blocking element is displaced by the actuator between a blocking position and a release position. In the blocking position, the at least one blocking element deforms the at least one line section in order to block the at least one flow path.

17 Claims, 4 Drawing Sheets

(51) Int. Cl.
*F16K 31/10* (2006.01)
*F16K 7/04* (2006.01)
*A61M 5/14* (2006.01)

(56) References Cited

U.S. PATENT DOCUMENTS

| | | | | |
|---|---|---|---|---|
| 3,683,962 | A * | 8/1972 | Good | F16K 11/168 |
| | | | | 137/868 |
| 3,861,421 | A * | 1/1975 | Thompson | F16K 7/06 |
| | | | | 137/636.4 |
| 3,918,490 | A * | 11/1975 | Goda | F16K 7/065 |
| | | | | 137/240 |
| 3,991,788 | A * | 11/1976 | Kull | B67D 1/12 |
| | | | | 137/637.1 |
| 4,061,142 | A * | 12/1977 | Tuttle | A61M 1/30 |
| | | | | 251/9 |
| 4,259,985 | A * | 4/1981 | Bergmann | F16K 7/045 |
| | | | | 137/595 |
| 4,491,156 | A * | 1/1985 | Lee, II | F16K 7/045 |
| | | | | 137/595 |
| 4,575,007 | A * | 3/1986 | Groth | B01F 15/0429 |
| | | | | 137/863 |
| 5,205,323 | A * | 4/1993 | Baker | F16K 31/105 |
| | | | | 137/625.44 |
| 6,003,552 | A * | 12/1999 | Shank | F16K 7/16 |
| | | | | 137/625.44 |
| 6,726,173 | B2 * | 4/2004 | Hettinger | F16K 31/0682 |
| | | | | 251/129.17 |
| 2008/0006336 | A1 * | 1/2008 | Bai | F16K 7/14 |
| | | | | 137/625.44 |
| 2009/0146091 | A1 * | 6/2009 | Ams | F16K 11/052 |
| | | | | 251/129.16 |
| 2010/0064900 | A1 * | 3/2010 | Reyhanloo | A47J 31/4485 |
| | | | | 99/300 |
| 2011/0095212 | A1 | 4/2011 | Brieske | |
| 2013/0119284 | A1 | 5/2013 | Fukano et al. | |
| 2015/0088055 | A1 * | 3/2015 | Tan | A61M 1/3659 |
| | | | | 604/33 |
| 2015/0232798 | A1 * | 8/2015 | Zhou | C12M 29/00 |
| | | | | 435/289.1 |

FOREIGN PATENT DOCUMENTS

| | | | |
|---|---|---|---|
| EP | 0691493 A1 * | 1/1996 | F16K 7/068 |
| EP | 2 314 344 | 4/2011 | |
| WO | WO 2009/149137 | 12/2009 | |

* cited by examiner

DEVICE FOR CONTROLLING FLUID MEDIA AND USE OF A MOLDED PART IN SUCH A DEVICE

CROSS-REFERENCE TO A RELATED APPLICATION

The invention described and claimed hereinbelow is also described in European Patent Application 14 190 865.7, filed on Oct. 29, 2014. The subject matter of the European Patent Application is incorporated herein by reference and, provides the basis for a claim of priority of invention under 35 U.S.C. 119(a)-(d).

BACKGROUND OF THE INVENTION

The present invention relates to a device for controlling fluid media, in particular a directional control valve, which includes at least one flow path that extends between at least two connections. The device includes a control unit equipped with an actuator that is coupled to at least one blocking element, which, in a blocking position, blocks the at least one flow path. Furthermore, the present invention relates to the use of a molded part in such a device, in particular in a directional control valve.

Devices of the aforementioned type, in particular, directional control valves, are known. For example, compact solenoid valves designed for use in the field of medical technology or analysis technology are known. Such valves are supposed to be suitable, in principle, for controlling aggressive or even highly aggressive media. This can include highly reactive media. Suitability for media requiring a high level of purity or, in general, sensitive media, is supposed to be given as well.

In this context, it is often preferable to provide a structural separation between flow paths, which are designed to conduct the media, and movable components of the valve, which can act on the flow paths, in order to selectively block or release a path for the media. One approach for this is to provide a so-called separation membrane, which is disposed between an actuator of the valve and at least one flow path and preferably forms at least one part of a line section. Such a separation membrane can therefore bring about, at least in sections, a hermetic (material) separation between the flowing media and the actuator.

It has been shown, however, that deposits, corrosion or even component damage, which is traced back to the media used, can also occur in valves provided with separation membranes in the manner described above. This can increase the amount of cleaning and maintenance and even repair, if necessary, that is required. Conversely, a contamination of the media can also pose a threat, and so a considerable amount of effort is required for cleaning, disinfection, or even sterilization.

Furthermore, it has been shown that in the case of compact valves, in particular, which is referred to basically as so-called microvalves, the required cleaning, maintenance and/or repair work is difficult due to poor accessibility. The tendency toward increasingly more compact valves in the medical field, in the laboratory field, and in the field of analysis would further increase these disadvantages.

Valves, which are also suitable for aggressive or even highly aggressive media, often require the use of high-quality materials at least in the flow-guiding parts thereof. The high-quality materials are stainless steel or special plastics, for example, which have an at least adequate resistance to media.

SUMMARY OF THE INVENTION

The present invention overcomes shortcomings of known arts, such as those mentioned above.

In an embodiment, the invention provides a device for controlling fluid media, for example, a directional control valve, which has a compact design and requires little installation space.

The invention also provides a device for controlling fluid media, which is suitable for use in the field of analysis technology and/or medical technology.

The invention also provides a device for controlling fluid media, which is suitable for controlling and/or regulating aggressive or even highly aggressive media.

The invention also provides a device for controlling for controlling fluid media, which is easily cleaned and maintained and, in addition, is designed to be as easy to repair as possible.

The invention also provides a device for controlling for controlling fluid media, which is produced at low cost, wherein it is preferably possible to use near-net-shape manufacturing processes, which can reduce the amount of production and machining required.

The invention also provides methods embodying exemplary uses of a molded part in a device for controlling fluid media, for example, in a directional control valve.

The invention also provides a device for controlling fluid media, for example, a directional control valve, having a molded part made from an elastomeric material, in which at least one line section is formed. The line section connects at least two connections to one another, between which at least one flow path extends. The device has a control unit, which includes an actuator that is coupled to at least one blocking element. The at least one blocking element is displaced by the actuator between a blocking position and a release position. The at least one blocking element, in the blocking position, deforms the at least one line section in order to block the at least one flow path.

Preferably, the molded part is made from the elastomeric material that enables a complete separation of the fluids used from the remaining components of the device. The device is therefore suitable for controlling and/or regulating media, for example fluids, which are aggressive, reactive, sensitive, or require a high level of purity, since these definitely do not come into contact with any components other than the molded part. In other words, a complete insulation or hermetic separation between the media and further parts of the device is brought about. All the flow paths that the device has can extend completely along the line sections provided by the molded part.

The device is designed to be extremely compact. The hermetic separation between the media to be controlled and the remaining components makes it possible to design the components, for example, the control unit and the actuator, in a way that is optimal with respect to the dimensions of the device. When designing these components, there is no need to make special allowances for the properties of the media. In other words, the device is produced using low-cost materials and simple component geometries, whereby cost advantages in production and, for example, installation-space advantages can result. Furthermore, any efforts required to clean, disinfect or even sterilize flow-guiding parts of the device is substantially minimized.

The molded part provides at least one continuous or continuously designed flow path and makes this entirely from elastomeric material. As compared to the use of so-called separation membranes in conventional devices, this results in the effect that there is no fear that the media will come into contact with other components.

When separation membranes are used in conventional devices, at least subsections of the flow paths are formed by other components and must therefore be suitable for the media used. This makes it necessary to use expensive materials, such as stainless steel or similar material. In the case of conventional directional control valves for aggressive, sensitive, or highly pure media, for example, which are based on the use of separation membranes, this results in increased efforts for the provision of materials and for production. The need for such separation membranes is avoided by use of the present invention.

The use of at least one molded part, which provides at least one continuous flow path, furthermore makes it possible to easily replace a molded part in the event of wear and in the event of any type of damage. The molded part can therefore be considered to be a replaceable part or a wear part. The device is easily designed for a simple replacement of the molded part. In this way, the device can also be suitable, for example, for use with different types of media if molded parts allocated to the particular medium are kept in reserve accordingly. Since each of the various media would contact only the corresponding molded part, it is not necessary to carry out any particular type of cleaning, sterilization, or any other type of upkeep when switching between different media.

The elastomeric material is, for example, silicone or a silicone-based material. Furthermore, the use of fluoroplastics is conceivable, for example, polytetrafluoroethylene (PTFE). For example, materials having good thermal resistance and, for example, good chemical resistance is used. It is understood that, in addition to the aforementioned materials, other materials are conceivable, which have sufficiently elastic behavior and have an at least sufficient resistance with respect to the media used. Alternative materials for the molded part is, for example, fluorinated rubber (FKM or KPM), perfluorinated rubber (FFKM or FFPM), ethylene propylene diene rubber (EPDM) and similar elastomeric materials. Furthermore, various thermoplastic elastomers are conceivable.

It is understood that the elastomeric materials used can be provided with additives, coatings and/or surface treatments in a suitable manner in order to make these even better suited for the intended use. For example, the molded part is produced using a primary shaping manufacturing process. This is, for example, an at least near-net-shape manufacturing process. In this way, even relatively complex molded parts can be produced relatively easily. For example, the molded part is designed in such a way that the at least one flow path formed herein provides substantially constant flow cross-sections in the unloaded state.

The actuator is, for example, a magnetic actuator. The actuator is therefore designed as an electromagnetic actuator and includes a movable armature, for example a pivot armature, which, in the activated state, acts on the at least one blocking element. In an alternative way, the actuator can include a pull-in armature. To this end, the actuator is designed to provide a defined displacement or a defined force when transitioning between an inactive and an active (energized) state.

The at least one blocking element can act from the outside on the line section to be blocked, for example in the manner of a tube clamp. In this way, the line section is elastically deformed in such a way that the flow section formed in the line section is closed or blocked in the blocking position, in order to halt the flow of the medium.

According to another embodiment, the molded part includes three or more connections, between which at least two flow paths extend, wherein the actuator is coupled to at least two blocking elements in order to selectively block or release at least one flow path of the at least two paths. In other words, the device is designed as a 3-position directional control valve. The connections can be referred to, for example, as COM, NC and NO. The connection referred to as COM is a common connection, for example a common supply line or discharge line. The NC (normally closed) connection is usually the connection that is blocked in the inactive state of the actuator. The NO (normally open) connection is usually the connection that is open in an idle state of the actuator. In all, the device can therefore have at least two discrete switching positions, in which either the flow path between the COM and NC connections or the flow path between the COM and NO connections is defined as being blocked. It is understood that at least a third state, in which both flow paths are blocked, is also conceivable.

According to another embodiment, the device furthermore has a coupling mechanism, which is driven by the actuator, wherein the coupling mechanism mechanically couples the first blocking element and the second blocking element to one another, wherein the first blocking element is in the blocking position when the second blocking element is in the release position, and wherein the first blocking element is in the release position when the second blocking element is in the blocking position. In this way, a plurality of discrete states is brought about by only one actuator. Furthermore, a forced coupling is implemented in order to increase the functional reliability and fault tolerance of the device.

For the blocking elements, a stop is furthermore provided in the device, for example on the housing side, in order to prevent overloads or excessive stresses, for example in the blocking position. In this way, an excessive deformation of the molded part, for example, or an excessive deflection of the blocking elements is prevented.

According to another embodiment, the first blocking element and the second blocking element are coupled to one another in such a way that the first blocking element and the second blocking element, at least in an intermediate position between the blocking position of the first blocking element and the blocking position of the second blocking element, simultaneously block the flow paths assigned to these blocking elements. In this way, a third defined position or a third switching state, in which both flow paths are blocked, is brought about. This has the effect that the transition between the switching states, in each of which a flow path is released, can take place without overlap. This can further increase the operational reliability and, for example, the dosing accuracy. Furthermore, the medium is effectively prevented from overflowing out of one flow path and into another flow path.

For example, the device is designed, for example in the manner of a sluice, to transfer a blocking element in the blocking position into the release position only after the other blocking element has moved out of its release position and into its blocking position.

This embodiment also is the subject matter of an independent invention and can therefore be used without requiring a molded part according to the aforementioned aspects. It is recommended, however, to couple such a coupling mechanism indirectly to the particular flow paths or line sections, for example, with deformable, sufficiently elastomeric materials connected therebetween. Provided the coupling mechanism is coupled to blocking elements, which can indirectly block the flow paths via deformable materials, the requirement on production tolerances and/or assembly tolerances is reduced, and so the desired functionality is also achieved when the blocking elements are merely positioned or moved with sufficient accuracy.

According to another embodiment, the device furthermore includes a tensioning element, which is coupled to the coupling mechanism and acts upon or forces the first blocking element and the second blocking element, at least in the intermediate position between the blocking position of the first blocking element and the blocking position of the second blocking element, in the direction of the line sections assigned to these blocking elements. The tensioning element, in the intermediate position, can therefore act on the blocking elements in order to block both line sections, at least in sections. This can bring about the desired, overlap-free transition. The tensioning element can also be referred to as a stop spring, for example.

According to another embodiment, at least one blocking element of the coupling mechanism is coupled to a housing part of the device via a material joint. In other words, the blocking element is produced as an integral component of the housing part. This can further reduce the production complexity and, for example, the amount of assembly required. The blocking element is pivotably mounted on the housing part by the material joint. This can further contribute to the miniaturization of the device.

In an embodiment, the coupling mechanism is designed as a scissor mechanism, wherein the first blocking element is assigned to a first scissor lever and the second blocking element is assigned to a second scissor lever, which are hingedly coupled to one another, for example. This measure has the effect that one of the two scissor levers is acted upon by means of only one actuator, wherein the coupling between the two scissor levers induces a corresponding movement of the second scissor lever. For example, at least one of the two scissor levers is integrally bonded to a housing part of the device.

According to another embodiment of the coupling mechanism designed as a scissor mechanism, the first blocking element and the second blocking element are tensioned relative to one another in order to induce a relative pivoting between the first blocking element and the second blocking element, wherein, for example, the first scissor lever is acted upon in the direction of a first stop and the second scissor lever is acted upon in the direction of a second stop on the actuator, for example, on an armature of the actuator. In other words, a tensioning element is provided, which is accommodated between the two scissor levers of the scissor mechanism and, together with the two stops, brings about a defined relative position between the scissor levers and, therefore, the blocking elements. This can further increase the switching accuracy and precision. This measure can assist in this measure the transition between the two extreme positions, in each of which a blocking element is in the blocking position, taking place without overlap. For this purpose, the tensioning element can act indirectly or directly on a pivot axis of the scissor mechanism.

According to another embodiment, the coupling mechanism is designed as a rocker-arm mechanism and is provided with a rocker arm, which has a rigid connection between the first blocking element and the second blocking element and can pivot about a pivot axis in order to transfer either the first blocking element or the second blocking element into the blocking position. According to this embodiment, the coupling mechanism is designed, in principle, in the manner of a (double) rocker.

According to a refinement of this embodiment, the rocker arm is coupled to the pivot axis via a slot so as to be longitudinally displaceable and pivotable, wherein the rocker arm is tensioned in the direction toward the molded part, wherein the rocker arm is movable relative to the pivot axis, for example, by a longitudinal displacement. According to an exemplary refinement, a tensioning element acts upon the rocker arm in the direction of the molded part. The rocker can therefore be pivoted by the actuator in order to force either the first blocking element or the second blocking element into the blocking position. During the transition between the two extreme positions, it is ensured by the tensioning element, however, that the transition will be free of overlap. For this purpose, the rocker arm is at least minimally "deflectable" by the slot-pivot axis pairing, in order to enable both blocking elements to be simultaneously brought into an engagement with the molded part in a blocking manner.

According to another embodiment, the device furthermore comprises a restoring element, for example, a restoring spring, wherein the restoring element acts upon the coupling mechanism in the direction of a neutral position when the actuator is inactive. In the neutral position, a flow can result, for example between the COM connection and the NO connection, wherein the flow path extending between the COM connection and the NC connection is blocked. The first blocking element can therefore be in the blocking position.

According to another embodiment of the device, the molded part is designed as a replaceable insert part, wherein the molded part is designed as a molded tube, for example, on the basis of a silicone material or a fluoroplastic, and wherein grommets adjacent to the connections, for example, are integrally formed on the molded part. The grommets provide a connection geometry for external lines. Furthermore, the grommets ensure an orientation of the molded part on the device. The molded part is therefore easily replaced, wherein an intended position and an intended orientation of the molded part necessarily results, with certainty, by the arrangement and design of the grommets.

According to another embodiment, the device furthermore includes at least a first housing part and a second housing part, which is connected to one another in a locking manner, for example, by a snap-fit assembly. The actuator is accommodated on a first housing part. One of the housing parts can have a defined receiving contour for accommodating the molded body in an interlocking manner. For example, the first housing part or the second housing part, for example, both housing parts, are made from a plastic material. This is, for example, polyoxymethylene (POM), polyamide (PA), polymethylmethacrylate (PMMA) or similar plastic materials, which are suitable for processing by means of injection molding. For example, the molded part is made from a sterilizable material. The molded part is easily removed in order to be delivered to a cleaning process or even to a sterilization process.

For example, the second housing part is easily accessible in order to further simplify the replacement of the molded part. Since the potentially aggressive or highly sensitive media are completely separated from the housing parts by the molded part, the housing parts can be made from materials which are favorable and are easily processed. For example, it is not necessary to provide flow channels for flow guidance, which are made from stainless steel, in the housing parts. Furthermore, at least one stop for limiting the deflection of at least one of the blocking elements, for example, both blocking elements, is formed on the second housing part.

According to another embodiment of the device, the actuator is designed as an electromagnetic actuator. The actuator comprises a C-shaped or U-shaped yoke, which is coupled to an armature, for example, a pivot armature or a hinged armature. The yoke is coupled to a plurality of coils, for example to three coils, each of which is assigned to a leg or section of the yoke. The C-shaped or U-shaped yoke has three legs, for example, each of which can accommodate a coil. In this way, the magnetic force is maximized for given maximum dimensions of the actuator.

It is understood that, on the basis of a device designed according to at least one of the aforementioned aspects, a valve system is created, which has a plurality of actuators and, if necessary, also a plurality of molded parts. It is understood that a complexly designed molded part, which has more than three connections and corresponding flow paths, also is provided. Such a molded part is coupled to a plurality of blocking elements, which is controlled by a plurality of actuators in a corresponding manner.

With respect to the use, this and further problems are solved by a use of a molded part made from an elastic material as a replaceable insert part in a device for controlling fluid media. The device has a receptacle for the molded part, wherein at least one line section, which connects at least two connections to one another, is formed in the molded part, between which connections at least one flow path extends. The device has a control unit, which includes an actuator that is coupled to at least one blocking element. The at least one blocking element is displaced by the actuator between a blocking position and a release position. The at least one blocking element, in the blocking position, deforms the at least one line section in order to block the at least one flow path. By way of example, the use is implemented with a device for controlling fluid media, which is designed according to at least one of the above-described aspects.

The molded part is suitable as a replaceable insert part for a directional control valve, for example a multiway valve. The molded part is easily replaced in response to wear or damage, for example; furthermore, the device is easily adapted to various media by replacing the molded part without the need for time-consuming cleaning or even sterilization.

It is understood that the features mentioned above and which are described in the following may be used not only in the combination described, but also in other combinations or alone, without departing from the scope of the present disclosure.

BRIEF DESCRIPTION OF THE DRAWINGS

Further features and advantages of the invention will become apparent from the description of embodiments that follows, with reference to the attached figures, wherein.

DETAILED DESCRIPTION OF THE INVENTION

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
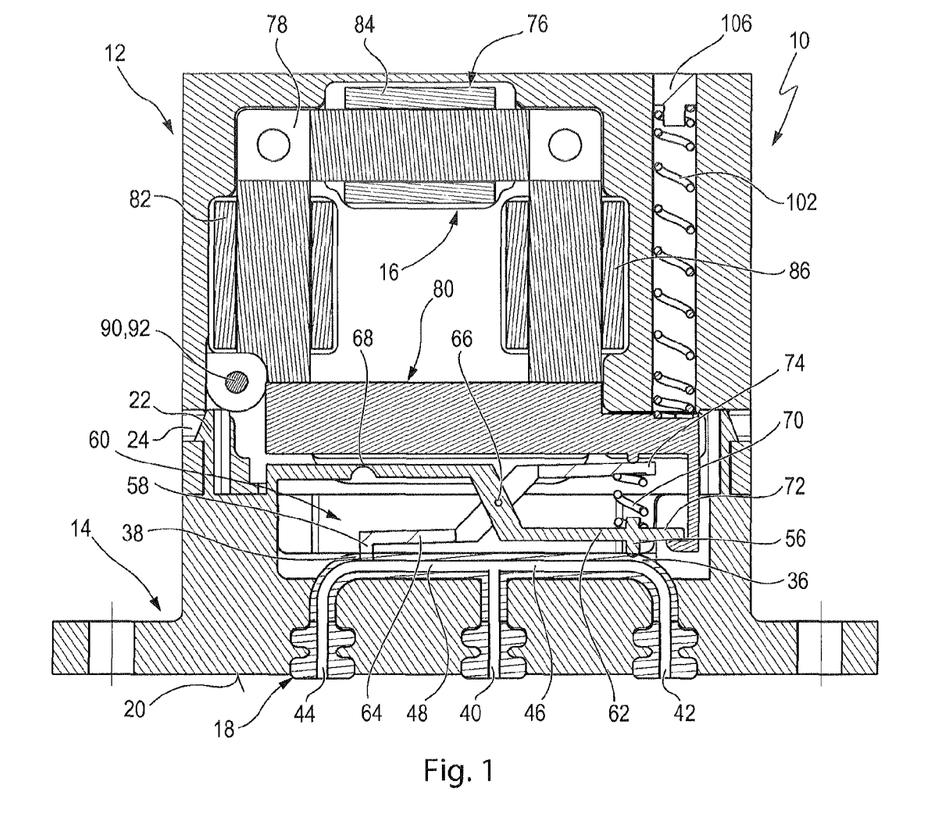
FIG. 1 depicts a longitudinal section through an exemplary embodiment of a device for controlling fluid media, according to the invention.
Figure 2:
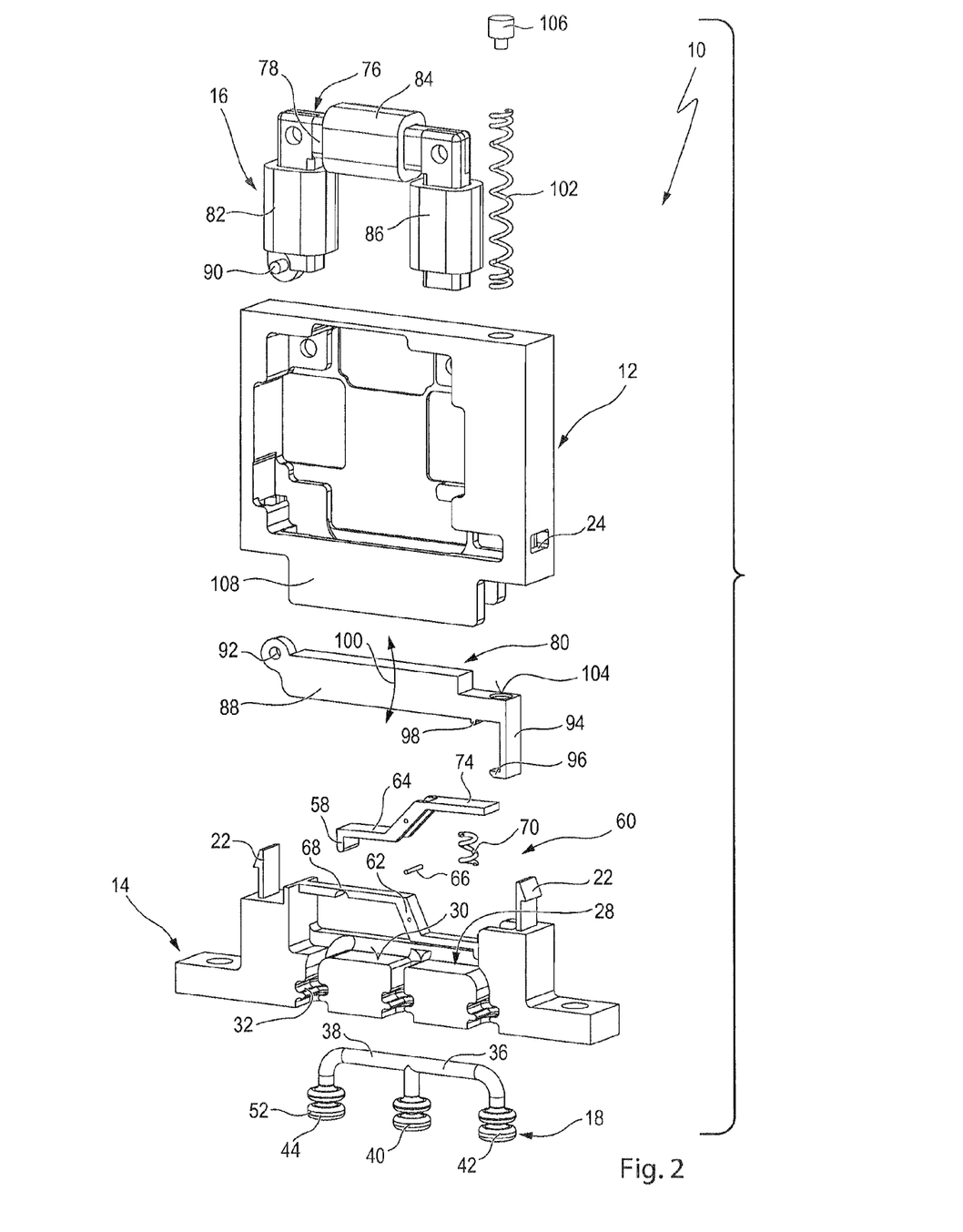
FIG. 2 presents a perspective exploded view of the device according to FIG. 1.

FIG. 1 shows a longitudinal section of a device 10 for controlling fluid media. An exploded view of the device 10 according to FIG. 1 is shown in FIG. 2. An alternative embodiment of a device 10' for controlling fluid media is shown in the longitudinal section according to FIG. 5 and in the corresponding exploded view according to FIG. 6. The devices 10, 10' are designed as valve systems, for example as so-called directional control valves. The devices 10, 10' in the embodiments according to FIGS. 1, 2 and 5, 6 are designed as 3/2-directional control valves by way of example. In other words, each device 10, 10' has three connections and two defined switching positions. Other embodiments are conceivable, of course, and can relate to the number of connections or the fluid paths extending between the connections and to the number of conceivable switching positions.

As shown in FIGS. 1 and 2, the device 10 has a first housing part 12 and a second housing part 14. The first housing part 12 is designed, for example, to accommodate a control unit 16, which can include a magnetic actuator, for example. The second housing part 14 is designed, for example, to accommodate a molded part 18, which is designed, for example, as a tube insert part. In at least some embodiments, the first housing part 12 is referred to as the upper part and the second housing part 14 is referred to as the lower part. It is understood that the corresponding assignments are provided merely as examples and are not intended to be limiting. An interface 20 for the installation or connection of the control device 10 is formed on the second housing part 14. In other words, the interface 20 includes a connecting plate, for example.

For example, at least the first housing part 12 or the second housing part 14 is produced as a cast part from a material, which is processed by injection molding, for example, from a thermoplastic. In this way, the housing parts 12, 14 are produced easily and at low cost in large numbers of parts. In an embodiment, the housing parts 12, 14 are joined to one another using a snap-fit assembly. For this purpose, at least one latch hook 22 is formed on one of the housing parts 12, 14, wherein the latch hook engages into a latch recess 24, which is provided on the other housing part 12, 14. In this way, the housing parts 12, 14 can be securely joined using a back-side snap-fit assembly. It is understood that the housing of the control device 10 also can have a different design and can be, for example, one-pieced, two-pieced, or three-pieced. Furthermore, an assignment of the control unit 16 and the molded part 18 to the housing parts 12, 14, respectively, which deviates from the representation according to FIG. 1, also is possible. The design shown in FIGS. 1 and 2 is the subject matter of exemplary embodiments.

FIG. 2 shows that the second housing part 14 is provided with a receiving contour 28 for the molded part 18. The receiving contour 28 includes an insert contour, into which the molded part 18 is inserted or placed in a defined manner. The receiving contour 28 has at least one flat piece 30, for example, two flat pieces 30, and at least one clamping groove or receiving groove 32. In all, the receiving contour 28 is produced, at least in sections, as a "negative" contour of the molded part 18. FIG. 2 further shows that the molded part 18 is introduced or inserted laterally into the receiving contour 28 of the second housing part 14. In all, the molded part 18 is easily and quickly replaced in this manner. This is carried out in the event of repair or wear. This is carried out primarily when a plurality of molded parts 18 are kept in reserve in order to control various fluids or media. In this way, the control device 10 is used to control or regulate various types of media, which can also include, for example, highly pure, sensitive, aggressive, highly aggressive, reactive, highly reactive, and generally reactive media.

FIG. 2 furthermore shows that the molded part 18 is substantially approximately W-shaped or m-shaped, wherein a first line section 36 and a second line section 38 are provided by way of example. The first line section 36 extends between a first connection 40, which can also be referred to as a COM connection, and a second connection 42, which can also be referred to as an NC connection. By way of example, the second line section 38 extends between the first connection 40 and a third connection 44, which can also be referred to as an NO connection. Each of the connections 40, 42, 44 can be assigned to one end of a leg of the "W" or the "m".

A flow path 46, 48 is defined between two of the connections 40, 42, 44 in each case. By way of example, a first flow path 46 extends between the first connection 40 and the second connection 42, cf. also FIG. 1. Correspondingly, a second flow path 48 extends between the first connection 40 and the third connection 44. The flow paths 46, 48 are located entirely within the molded part 18. Therefore, no other components of the control device 10 directly contact either one of the flow paths 46, 48. For example, the molded part 18 is designed in such a way that the flow paths 46, 48 have an at least substantially constant flow cross-section 50, cf. also FIG. 3. This applies, for example, for a neutral, unloaded state of the molded part 18.

FIG. 2 shows a grommet 52 assigned to at least one or each of the connections 40, 42, 44, which grommet is designed as an integral component of the molded part 18 or is integrally molded thereon. For example, the at least one grommet 52 is matched to the at least one receiving groove 32 of the receiving contour 28 in such a way that the molded part 18 is accommodated in a defined manner and at least partially in an interlocked manner. For this purpose, the at least one grommet 52 is inserted into the at least one corresponding receiving groove 32, wherein the line sections 36, 38 can come to rest against the flat pieces 30.

An important task of the control device 10 is to selectively release or block the flow paths 46, 48 (FIG. 1) defined by the molded part 18. For this purpose, the control device 10 comprises, by way of example, a first blocking element 56 and a second blocking element 58, which can also be referred to in general as clamps. The first blocking element 56 is assigned to the first line section 36 by way of example. Correspondingly, the second blocking element 58 is assigned to the second line section 38. The flow paths 46, 48 can be indirectly blocked by the blocking elements 56, 58. This means that the blocking elements 56, 58 do not need to come into direct contact with the flowing media in order to effectively block the flow paths 46, 48.

Figure 3:
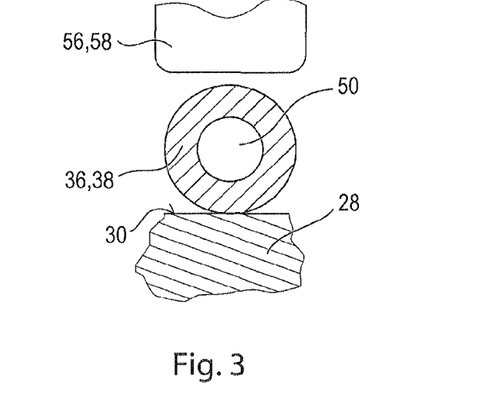
FIG. 3 depicts a schematically greatly simplified lateral section through a line section, which is blocked by a blocking element in a release position, as shown.
Figure 4:
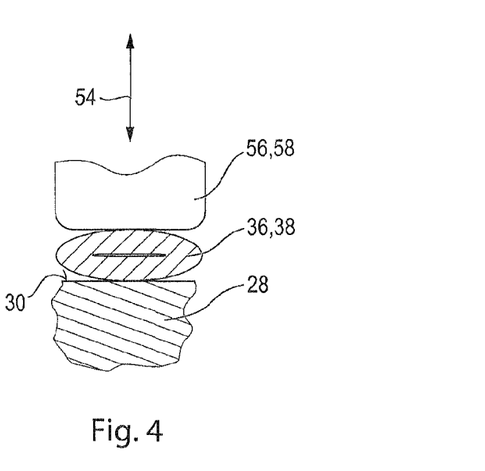
FIG. 4 presents another view of the line section according to FIG. 3, wherein the blocking element is in a blocking position.

Reference is made in this context to the schematic representations in FIGS. 3 and 4 by way of example. FIG. 3 shows a so-called release position of a blocking element 56, 58. FIG. 4 shows a so-called blocking position of a blocking element 56, 58. In the release position according to FIG. 3, the blocking element 56, 58 does not act or only unsubstantially acts on the line section 36, 38. The flow cross-section 50 is therefore entirely or nearly entirely available and the desired medium can flow through the corresponding line section 36, 38. In the blocking position illustrated in FIG. 4, the blocking element 56, 58 acts on the line section 36, 38 in order to close or block the flow cross-section 50. For this purpose, the blocking element 56, 58 acts on the line section 36, 38 with a defined force in order to deform the line section to such an extent that the flow cross-section 50 (cf. FIG. 3) is closed as sealingly as possible. The receiving contour 28 or the flat piece 30 thereof then functions as a counter bearing. The blocking element 56, 58 can therefore act on the line section 36, 38 in the direction of the flat piece 30. A required movement of the blocking element 56, 58 between the blocking position according to FIG. 4 and the release position according to FIG. 3 is indicated in FIG. 4 by a double arrow labeled with reference number 54. The control unit 16 of the control device 10 is coupled or can be coupled to the blocking elements 56, 58 in order to generate this movement or the force required to block the desired flow path 46, 48.

An exemplary embodiment of a coupling mechanism 60 is illustrated by reference once more to FIGS. 1 and 2, which coupling mechanism can connect the blocking elements 56, 58 to one another and can bring about a coupling between the control unit 16 and the blocking elements 56, 58. According to the embodiment of the control device 10 illustrated in FIGS. 1 and 2, the coupling mechanism 60 is a so-called scissor mechanism, which includes a first scissor lever 62 and a second scissor lever 64. The scissor levers 62, 64 are coupled to one another via a pivot axis 66. At least one of the scissor levers 62, 64 can be bonded to at least one of the housing parts 12, 14. The first scissor lever 62 is connected to the second housing part 14 via a material joint 68 by way of example. In other words, the first scissor lever 62 is produced as an integral component of the second housing part 14. The material joint 68 is designed as an intentional weakening in the material, by way of example, and permits a relative movement of the first pivot lever 62 with respect to the second housing part 14.

For example, it is clear from the representation according to FIG. 1 that the first scissor lever 62 and the second scissor lever 64 are coupled to one another via the pivot axis 66 so as to be crossed. By way of example, the first blocking element 56 is formed on the first scissor lever 62, which blocking element acts on the first line section 36. Correspondingly, the second blocking element 58 is formed on the first scissor. lever 64, which blocking element acts on the first line section 38. The blocking elements 56, 58 are formed as wall-type projections on the scissor levers 62, 64, which extend in the direction of the associated line sections 36, 38. The blocking elements 56, 58 can be at least chamfered or rounded on the ends thereof facing the line sections 36, 38 in order to "gently" act on the deformable line sections 36, 38.

The scissor levers 62, 64 are furthermore coupled to one another via a tensioning element 70, which are designed as a compression spring, for example. In the embodiment shown in FIG. 1, the tensioning element 70 acts on the scissor levers 62, 64 in such a way that the first blocking element 56 and the second blocking element 58 would be moved toward one another via corresponding pivot movements of the scissor levers 62, 64 if the scissor levers 62, 64 did not bear against contact sections 72, 74 and would not be accommodated in a sufficiently defined relative position with respect to one another. The tensioning element 70 is designed to act on the scissor levers 62, 64 in such a way that these have the tendency to rotate opposite one another about the pivot axis 66. The special design of the coupling mechanism 60 according to FIGS. 1 and 2 prevents excessive relative rotation, however.

The control unit 16 is designed to act on the coupling mechanism 60 in order to selectively block at least one of the line sections 36, 38 and, therefore, at least one of the flow paths 46, 48. For example, the control unit 16 includes an actuator 76, which are designed as an electromagnetic actuator, for example. The actuator 76 includes a yoke 78, which interacts with an armature 80. At least one coil 82, 84, 86 is accommodated on the yoke 78, by means of which coil the actuator 76 can be activated or energized in order to bring about a defined movement of the armature 80 relative to the yoke 78. The yoke 78 is C-shaped or U-shaped overall, by way of example, wherein a total of three coils 82, 84, 86 are provided, of which, for example, a first coil 82 is assigned to a first leg, a second coil 84 is assigned to a base, and a third coil 86 is assigned to a second leg of the yoke 78. Other designs are conceivable, of course. It is possible to provide a plurality of coils 82, 84, 86. In all, a considerable magnetic force can therefore also be induced in the case of a limited installation depth of the control device 10 (perpendicularly to the plane of view in FIG. 1). In this way, a design of the control device 10 can result in which the housing parts 12, 14, overall, have an approximately cuboid shape, in which the cuboid has a limited depth extension.

The armature 80 has a main body 88 and is designed as a so-called pivot armature, for example. The armature 80 has a pivot bearing 92, which can be coupled to a pivot axis 90, which is assigned to the yoke 78 of the actuator 76, for example. A conceivable pivot movement of the armature 80 about the pivot bearing 92 thereof or about the pivot axis 90 is indicated in FIG. 2 by a double arrow labeled with reference number 100.

The armature 80 is coupled to the coupling mechanism 60 in order to block the first flow path 46 between the connections 40, 42 in an inactive (de-energized) state of the actuator 76, and to block the second flow path 48 between the connections 40, 44 in an active (energized) state of the actuator 76. Two discrete states of the control device can therefore be brought about via the coupling mechanism 60 by only one actuator 76. According to one embodiment, the coupling mechanism 60 is furthermore designed such that, during the transition between these two states, the coupling mechanism brings about a transition state, at least in sections, in which both flow paths 46, 48 are simultaneously blocked. This permits an overlap-free transition between the two defined end states.

The coupling mechanism 60 is designed, in particular, to ensure that both blocking elements 56, 58 are at least briefly simultaneously in or near the blocking position thereof also during the transition between the blocking position of the first blocking element 56 and the blocking position of the second blocking element 58, in order to block both flow paths 46, 48 simultaneously.

In general, the main body 88 of the armature 80 is designed approximately in the manner of a bar or a rod, wherein the bar is designed to connect the two legs of the U or the C of the yoke 78 at the open ends thereof when the actuator 76 is in the energized state. In addition, the armature 80 according to the embodiment illustrated in FIGS. 1 and 2 comprises a retaining segment 94, which is formed on the end of the main body 88 facing away from the pivot bearing 92. A first stop 96 is formed on the retaining segment 94, which, in the joined state, contacts the first contact section 72 of the first scissor lever 62. The first stop 96 faces the bar-type main body 88 of the armature 80. A second stop 98, which is disposed opposite the first stop 96, is formed on the main body 88. In the joined state, the second stop 98 contacts the contact section 74 formed on the second scissor lever 64.

In other words, the first contact section 72 and the second contact section 74 act as a clamp, wherein the tensioning element 70 forces the contact sections 72, 74 and, therefore, the first scissor lever 62 and the second scissor lever 64 apart from one another and brings these to rest against the stops 96, 98. This design brings about a coupling of the scissor levers 62, 64 by way of example. As already described above, the scissor levers 62, 64 are coupled to one another in a crossed manner, for example in an "X" shape (similar to a saltire). The pivot movement or deflection of the armature 80 (reference number 100 in FIG. 2), which is induced by an activation or deactivation of the armature 76, brings about a lifting of the armature 80 away from a corresponding contact surface of the yoke 78 in the inactive state. This movement (according to the design in FIG. 1, approximately one rotation in the clockwise direction) is transferred via the stop 98 to the second contact section 74 of the second scissor lever 64 and ensures that the second scissor lever 64 is pivoted in such a way that the second blocking element 58 is moved away from the second line section 78. In the design according to FIG. 1, the pivot movement of the second scissor lever 64 takes place in the clockwise direction.

The deflection or displacement of the armature 80 is transferred to the first scissor lever 62 via the first contact section 72 by the tensioning element 70. As a result, the first blocking element 56 is moved in the direction of the first line section 36 in order to finally be capable of blocking this line section. Correspondingly, in the design according to FIG. 1, the first scissor lever 62 also rotates in the clockwise direction about the pivot axis 66 when the armature 80 lifts away the yoke 78. This movement, which takes place, for example, when the actuator 78 is deactivated or de-energized, is supported by a restoring element 102, which is designed as a restoring spring, for example. The restoring element 102 is accommodated on the first housing part 12, for example, in a recess for bore, for example, which is closed using a stopper 106. The restoring element 102 rests against the stopper 106. The restoring element 102 is designed as a compression spring, for example.

The restoring element 102 acts on a force application surface 104, which is formed on the armature 80. The restoring element can therefore bring about a defined neutral position of the armature 80 or the coupling mechanism 60 when the actuator 76 is inactive (de-energized). Provided the actuator 76 is activated (energized), the restoring force with which the restoring element 102 acts on the armature 80 must be overcome in order to bring the armature 80 to rest against the yoke 78. In the design according to FIG. 1, this movement of the armature takes place in the counterclockwise direction. Such a movement of the armature 80 also brings about a corresponding movement of the first scissor lever 62 and the second scissor lever 64 relative to the pivot axis thereof. The first blocking element 56 is therefore transferred out of the blocking position thereof into a release position. Conversely, the second blocking element 58 is transferred out of the release position thereof into the blocking position in order to block the second line section 38.

The particular design of the coupling mechanism 60 according to FIGS. 1 and 2 furthermore causes both line sections 36, 38 and, therefore, both flow paths 46, 48 to be at least temporarily simultaneously blocked during this transition. Since the first scissor lever 62 is pivotably accommodated on the second housing part 14 via a material joint 68 (and not via the pivot axis 66), the first scissor lever 62 pivots not only about the pivot axis 66 when the armature moves 80, but also about the material joint 68 or about a "virtual" pivot axis provided by the material joint 68. As a result, when the armature 80 moves, the pivot axis 66 is pivoted or displaced along with this armature and in the same direction thereof (but not necessarily to the same extent).

FIG. 1 shows, by way of example, an active (energized) state of the armature, in which the armature 80 contacts the yoke 78. In this state, the pivot axis 66 is in a position remote from the molded part 18. In the transition into the inactive (de-energized) state of the armature, in which the armature 80 is lifted away the yoke 78 or is deflected away therefrom, the pivot axis 66 also pivots relative to the material joint 68 and would thereby be moved toward the molded part 18. Due to this exemplary type of switching or the resultant displaceability of the pivot axis, during the transition between the two extreme positions of the armature 80, both line sections 36, 38 are briefly blocked by the blocking elements 56, 58 assigned thereto. By way of example, this state is brought about by a suitable configuration and design of the components of the coupling mechanism 60 without requiring a separate actuator 76 for this functionality, for example.

By way of example, the first housing part 12 further comprises at least one skirt or cover plate 108, which is disposed on the end of the first housing part 12 facing the second housing 14 (FIG. 2). The cover plate 108 assists in securing or fixing the molded part 18 in place on the second housing part 14. Furthermore, the cover plate 108 can at least sufficiently cover the coupling mechanism 60 and protect this against environmental influences.

Figure 5:
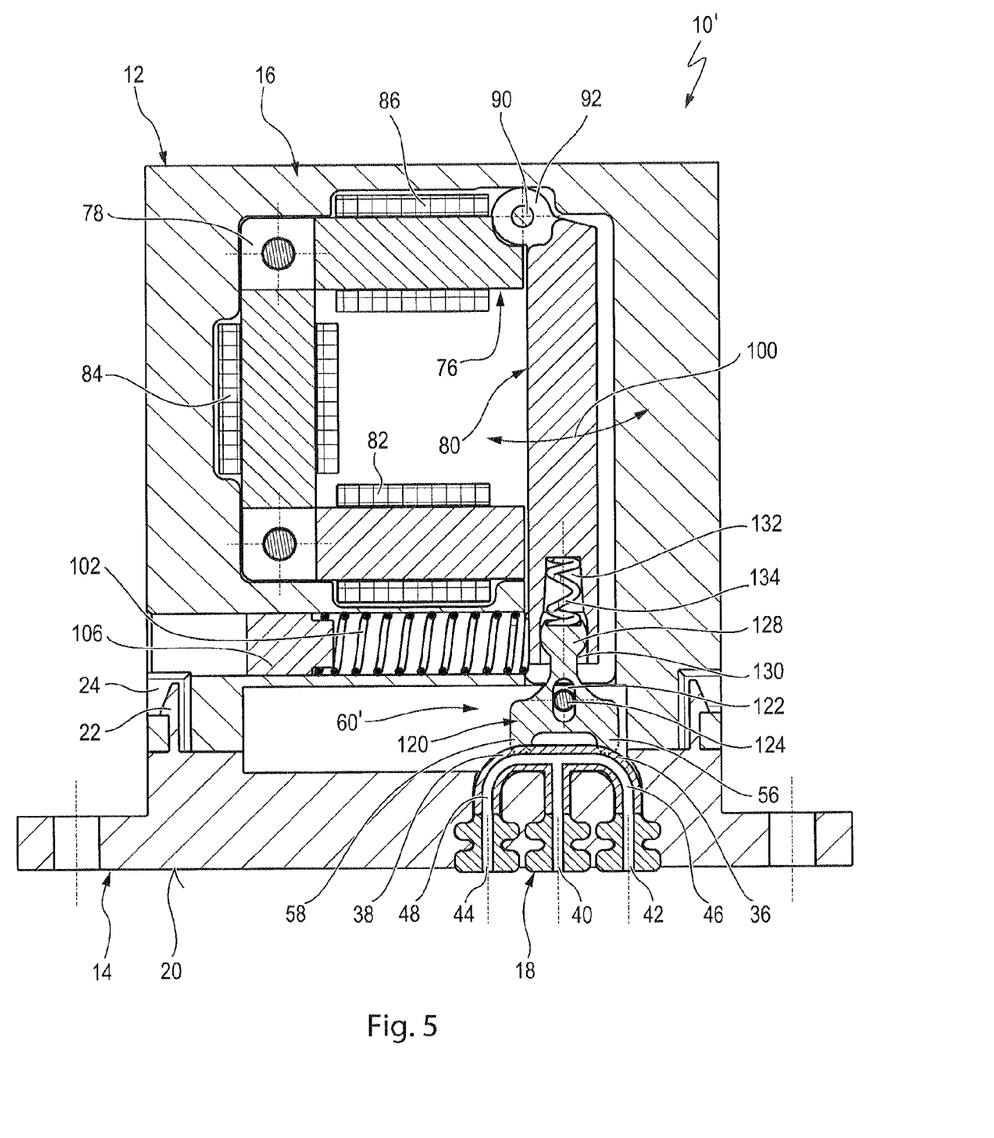
FIG. 5 depicts a longitudinal section through another embodiment of a device for controlling fluid media, according to the invention.
Figure 6:
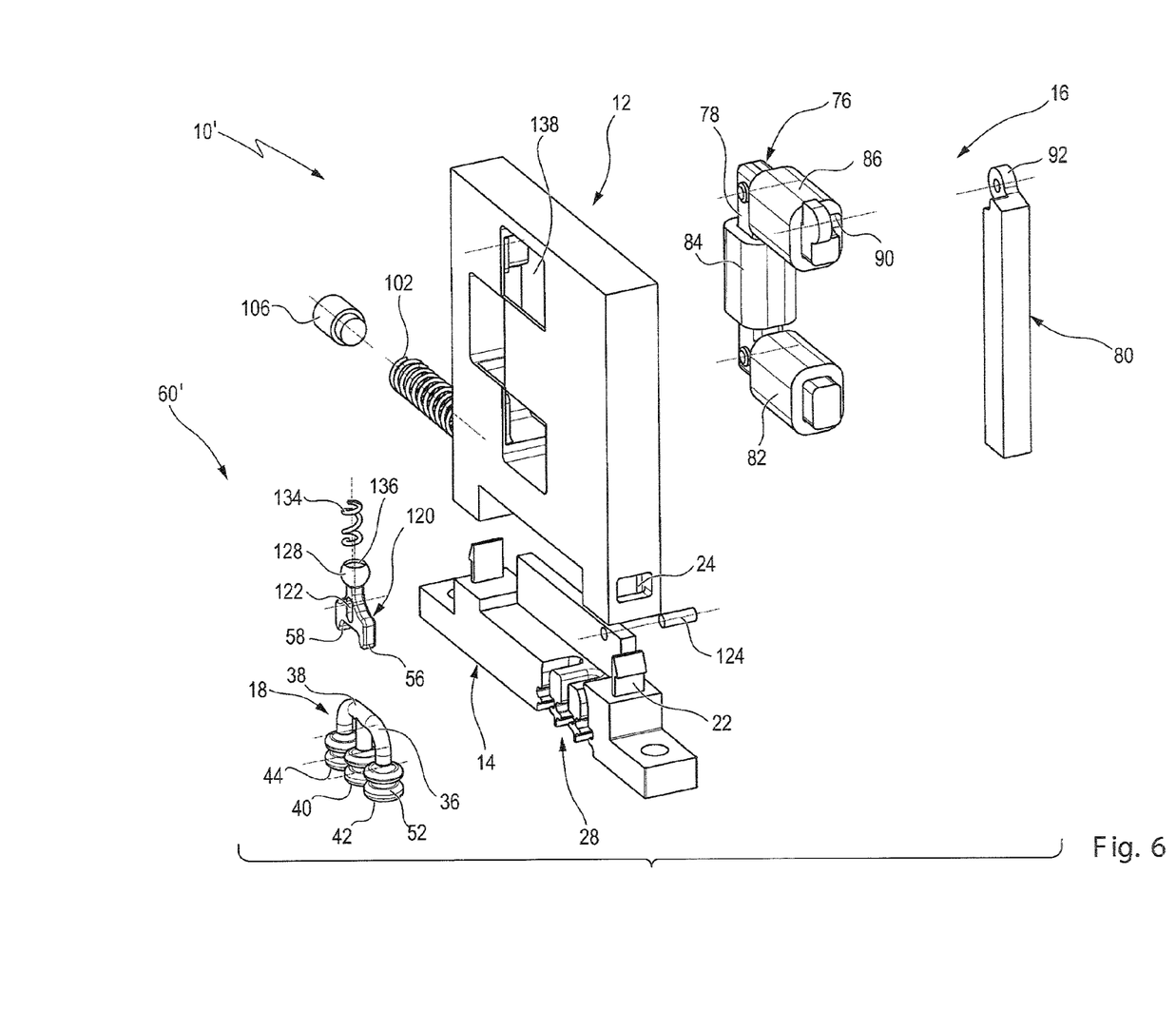
FIG. 6 presents a perspective exploded view of the device according to FIG. 5.

An alternative control device 10' is illustrated in FIGS. 5 and 6, which largely corresponds to the control device 10 illustrated in FIGS. 1 and 2 in terms of the functionality thereof. The distinguishing features are addressed in the following. The explanations of the embodiment according to FIGS. 1 and 2 is directly transferred provided there are no explicit explanations of the individual components of the embodiment of the control device 10' illustrated in FIGS. 5 and 6.

In the manner described above, the control device 10' is provided with housing parts 12, 14, wherein a first housing part 12 can receive or accommodate a control unit 16 and a second housing part 14 can receive or accommodate a molded part 18.

The control device 10' according to FIGS. 5 and 6 is designed as a directional control valve, for example, as a 3/2-directional control valve. The molded part 18 is accommodated on and supported against a receiving contour 28 of the second housing part 14. The molded part 18 comprises, by way of example, two line sections 36, 38 and three connections 40, 42, 44, between which the line sections 36, 38 extend. A first flow path 46 extends between the connections 40, 42. A second flow path 48 extends between the connections 40, 44. The housing parts 12, 14 are joined to one another via a snap-fit assembly, which includes at least one latch hook 22 and one latch recess 24.

In a generally described way, the control unit 16 comprises an electromagnetic actuator 76, which includes a C-shaped or U-shaped yoke 78, which is coupled to coils 82, 84, 86. The actuator 76 furthermore comprises an armature 80, which is deflectable relative to the yoke 78. The armature 80 is, by way of example, a pivot armature, which can pivot about a pivot axis 90, as well as the double arrow 100 in FIG. 5.

In the design according to FIG. 5, the armature 80 is pivoted or deflected in the counterclockwise direction when transitioning between an active (energized) state of the armature 76 into an inactive (de-energized) state. Conversely, when the actuator is activated (energized), the armature 80 moves in the opposite direction, in the clockwise direction, in order to contact the yoke 78.

In the design according to FIGS. 5 and 6 as well, the armature 80 is designed to act on a coupling mechanism 60', which is provided with blocking elements 56, 58, which can selectively block or release the first line section 36 or the second line section 38 in a defined manner. As already described above, the option also exists with the coupling mechanism 60' according to FIGS. 5 and 6 to at least briefly simultaneously block both line sections 36, 38 or the flow paths 46, 48 assigned thereto during the transition between these two switching positions.

The coupling mechanism 60 according to FIGS. 1 and 2 is designed as a scissor mechanism. In contrast thereto, the coupling mechanism 60' illustrated in FIGS. 5 and 6 is designed as a rocker-arm mechanism. The coupling mechanism 60' comprises a rocker arm 120, which is accommodated so as to be pivotable about a pivot axis 124, which is accommodated on at least one of the housing parts 12, 14, for example, on the second housing part 14. The rocker arm 120 can also be referred to as a rocker. In the embodiment shown in FIG. 5, the rocker arm 120 is pivoted in the clockwise direction in order to displace the first blocking element 56 out of the release position thereof and into the blocking position and simultaneously displace the second blocking element 58 out of the blocking position thereof and in the direction of the release position thereof. Both blocking elements 56, 58 are formed on the rocker arm 120, for example, as projections, which extend in the direction of the molded part 18.

The rocker arm 120 is provided with a recess, which is designed as a slot-type recess or a slot 122, for accommodation on the pivot axis 124. Therefore, the rocker arm 120 is not only pivotable about the pivot axis 124, but is also displaceable along the longitudinal extension of the slot 122 relative to the pivot axis 124. The design assists the control device 10 in at least briefly simultaneously blocking both flow paths 46, 48 during the transition between the two discrete switching states (either the first flow path 46 and the second flow path 48 is released).

The rocker arm 120 has a guide section 128, which is designed in the shape of a head, a sphere, or a spherical section, for example, on the end of said rocker arm facing away from the molded part 18. The guide section 128 is accommodated in a guide 130, which is formed, for example, as a cylindrical guide or a cylindrical recess, in the main body 88 of the armature 80. Pivoting the armature 80 in the counterclockwise direction therefore causes the rocker arm 120 to pivot in the clockwise direction about the pivot axis 124. This movement occurs, for example, when the actuator 76 is deactivated, i.e., de-energized, for example. In a known way, this movement is supported by a restoring element 102, which is designed as a restoring spring and acts upon the armature 80 with the restoring force thereof.

Furthermore, the coupling mechanism 60', which is designed as a rocker-arm mechanism, comprises a tensioning element 134, which is installed between the armature 80 and the rocker arm 120. The tensioning element 134 is designed, in principle, to act on the rocker arm 120 in the direction of an engagement with the molded part 18. The tensioning element 134 therefore brings about a longitudinal displacement of the rocker arm 120 relative to the pivot axis 124. The tensioning element 134 is accommodated in a spring receptacle 132 on the armature 80, which is formed in the armature 80 as an extension of the guide section 128 by way of example. Furthermore, a defined receptacle 136 for the tensioning element 134 designed as a spring, by way of example, is provided on the guide section 128 of the rocker arm 120.

The pure pivot movement of the rocker arm 120 is therefore superposed with a longitudinal displacement in order to bring both blocking elements 56, 58, in an intermediate position between the defined switching positions, in contact with the line sections 36, 38 assigned thereto with sufficient preload to simultaneously block both flow paths 46, 48.

FIG. 6 also shows that the first housing part 12, by way of example, is provided with defined recesses 138, each of which is assigned to one of the coils 82, 84, 84 of the actuator 76. This measure further reduces the depth extension or thickness extension of the control device 10. Furthermore, the recesses 138 assist in efficiently dissipating heat from the coils 82, 84, 86.

It is understood that the terms "in the clockwise direction", "in the counterclockwise direction" and the like, which are used within the scope of this disclosure, can each relate to a figure or to figures, which show an exemplary embodiment. Therefore, these terms must not be interpreted to be limiting. It is understood that, on the basis of the embodiments shown, a person skilled in the art can also readily arrive at embodiments and views which have an opposite layout, for example, and would therefore result in movements in the opposite direction. As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A device for controlling fluid media, comprising:
   a molded part made from an elastomeric material and including three connections, between which three connections first and second flow paths extend;
   a control unit, which includes an actuator; and
   first and second blocking element;
   wherein first and second line sections, which each connect two of the three connections to one another, are formed in the molded part;
   wherein each of the first and second flow paths extends between two of the three connections;
   wherein the actuator is coupled to the first and second blocking elements via a coupling mechanism and displaces each of the first and second blocking elements between a blocking position and a release position, to selectively block or release each of the first and second flow paths, respectively; and
   wherein the first and second blocking elements, in the blocking position, deform the respective first and second line sections to block the respective first and second flow paths;
   wherein the coupling mechanism is driven by the actuator and mechanically couples the first blocking element and the second blocking element to one another;
   wherein the first blocking element is in the blocking position when the second blocking element is in the release position;
   wherein the first blocking element is in the release position when the second blocking element is in the blocking position;
   wherein the coupling mechanism is designed as a scissor mechanism; and
   wherein the first blocking element is assigned to a first scissor lever of the scissor mechanism and the second blocking element is assigned to a second scissor lever of the scissor mechanism.

2. The device according to claim 1, wherein the first blocking element and the second blocking element are coupled to one another in such a way that the first blocking element and the second blocking element, at least in an intermediate position between the blocking position of the first blocking element and the blocking position of the second blocking element, simultaneously block the flow paths assigned to these blocking elements.

3. The device according to claim 2, further comprising a tensioning element that is coupled to the coupling mechanism and acts upon the first blocking element and the second blocking element, at least in the intermediate position between the blocking position of the first blocking element and the blocking position of the second blocking element, in the direction of the line sections assigned to these blocking elements.

4. The device according to claim 1, further comprising a housing part, on which a material joint is accommodated;
   wherein at least one of the first blocking element and the second blocking element is coupled to the housing part via the material joint.

5. The device according to claim 1, wherein the first scissor lever and the second scissor lever are hingedly coupled to one another.

6. The device according to claim 1, further comprising a tensioning element that is coupled to the first scissor lever and the second scissor lever to act on the first blocking element and the second blocking element with a preload, wherein the first blocking element and the second blocking element are preloaded relative to one another to bring about a relative pivoting between the first blocking element and the second blocking element.

7. The device according to claim 6, wherein the first scissor lever is preloaded in the direction of a first stop; and wherein the second scissor lever is preloaded in the direction of a second stop on the actuator.

8. The device according to claim 1, further comprising a restoring element; wherein the restoring element acts on the coupling mechanism in the direction of a neutral position when the actuator is in a non-activated state.

9. The device according to claim 1, wherein the molded part is a replaceable insert part.

10. The device according to claim 9, wherein the molded part is a molded tube made of a silicone material or a fluoroplastic; and wherein grommets adjacent to the connections are formed on the molded part.

11. The device according to claim 1, further comprising at least a first housing part and a second housing part; wherein the actuator is accommodated on the first housing part; and wherein the second housing part has a defined receiving contour for the interlocking accommodation of the molded part.

12. The device according to claim 1, wherein the actuator is as an electromagnetic actuator and includes a C-shaped or U-shaped yoke that is coupled to an armature; and wherein the yoke is coupled to a plurality of coils, each of which is assigned to a leg of the yoke.

13. The device according to claim 1, further comprising:
a receiving contour for the molded part;
wherein the molded part is a replaceable insert part.

14. A device for controlling fluid media, comprising:
a molded part made from an elastomeric material and including three connections, between which three connections first and second flow paths extend;
a control unit, which includes an actuator; and
first and second blocking element;
wherein first and second line sections, which each connect two of the three connections to one another, are formed in the molded part;
wherein each of the first and second flow paths extends between two of the three connections;
wherein the actuator is coupled to the first and second blocking elements via a coupling mechanism and displaces each of the first and second blocking elements between a blocking position and a release position, to selectively block or release each of the first and second flow paths, respectively; and
wherein the first and second blocking elements, in the blocking position, deform the respective first and second line sections to block the respective first and second flow paths;
wherein the coupling mechanism is driven by the actuator and mechanically couples the first blocking element and the second blocking element to one another;
wherein the first blocking element is in the blocking position when the second blocking element is in the release position;
wherein the first blocking element is in the release position when the second blocking element is in the blocking position;
wherein the coupling mechanism is a rocker-arm mechanism and includes a rocker arm that has a rigid connection between the first blocking element and the second blocking element;
wherein the rocker arm can pivot about a pivot axis to transfer either the first blocking element or the second blocking element into the blocking position; and
wherein the rocker arm includes a slot and is coupled to the pivot axis via the slot to be longitudinally displaceable and pivotable.

15. The device according to claim 14, wherein the rocker arm is preloaded in the direction toward the molded part; and wherein the rocker arm is moved toward the molded part and away from the molded part via a longitudinal displacement relative to the pivot axis.

16. A multiway valve for controlling fluid media, comprising:

a molded part made from an elastomeric material and including three connections, between which three connections extend first and second flow paths;
a control unit, which includes an electromagnetic actuator; and
a coupling mechanism, which includes a first blocking element and a second blocking element;
wherein the first blocking element is assigned to a first line section and the second blocking element is assigned to a second line section of the molded part;
wherein the coupling mechanism is driven by the actuator and; mechanically couples the first blocking element and the second blocking element to one another;
wherein the electromagnetic actuator displaces the first blocking element and the second blocking element between a blocking position and a release position;
wherein the first blocking element and the second blocking element, in the respective blocking position, deform the respectively assigned line section to block one of the two flow paths;
wherein the first blocking element is in the blocking position when the second blocking element is in the release position;
wherein the first blocking element is in the release position when the second blocking element is in the blocking position;
wherein the coupling mechanism is designed as a scissor mechanism; and
wherein the first blocking element is assigned to a first scissor lever of the scissor mechanism and the second blocking element is assigned to a second scissor lever of the scissor mechanism.

17. A multiway valve for controlling fluid media, comprising:
a molded part made from an elastomeric material and including three connections, between which three connections extend first and second flow paths;
a control unit, which includes an electromagnetic actuator; and
a coupling mechanism, which includes a first blocking element and a second blocking element;
wherein the first blocking element is assigned to a first line section and the second blocking element is assigned to a second line section of the molded part;
wherein the coupling mechanism is driven by the actuator and
mechanically couples the first blocking element and the second blocking element to one another;
wherein the electromagnetic actuator displaces the first blocking element and the second blocking element between a blocking position and a release position;
wherein the first blocking element and the second blocking element, in the respective blocking position, deform the respectively assigned line section to block one of the two flow paths;
wherein the first blocking element is in the blocking position when the second blocking element is in the release position;
wherein the first blocking element is in the release position when the second blocking element is in the blocking position;
wherein the coupling mechanism is a rocker-arm mechanism and includes a rocker arm that has a slot and a rigid connection between the first blocking element and the second blocking element;

wherein the rocker arm can pivot about a pivot axis to transfer either the first blocking element or the second blocking element into the blocking position;
and wherein the rocker arm is coupled to the pivot axis via the slot to be longitudinally displaceable and pivotable.

* * * * *